United States Patent
Skiera et al.

(10) Patent No.: US 10,391,327 B2
(45) Date of Patent: Aug. 27, 2019

(54) ELECTRODE ARRANGEMENT FOR PLASMA TREATMENT AND DEVICE FOR PRODUCING A TRANSCUTANEOUS CONNECTION

(71) Applicant: OTTO BOCK HEALTHCARE GMBH, Duderstadt (DE)

(72) Inventors: Richard Skiera, Vienna (AT); Michael Meyer, Falkensee (DE); Dirk Wandke, Heilbad Heiligenstadt (DE); Matthias Kopp, Gieboldehausen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 94 days.

(21) Appl. No.: 14/417,479

(22) PCT Filed: Aug. 6, 2013

(86) PCT No.: PCT/DE2013/000437
§ 371 (c)(1),
(2) Date: Jan. 26, 2015

(87) PCT Pub. No.: WO2014/023281
PCT Pub. Date: Feb. 13, 2014

(65) Prior Publication Data
US 2015/0202452 A1 Jul. 23, 2015

(30) Foreign Application Priority Data

Aug. 7, 2012 (DE) .................... 10 2012 015 483

(51) Int. Cl.
*A61F 2/78* (2006.01)
*A61N 1/44* (2006.01)
(Continued)

(52) U.S. Cl.
CPC ............. *A61N 1/44* (2013.01); *A61F 2/0077* (2013.01); *A61F 2/78* (2013.01); *A61L 2/0011* (2013.01);
(Continued)

(58) Field of Classification Search
CPC ........... A61N 1/44; A61F 2/78; A61L 2/0017; H05H 2001/2414; H05H 2001/2418;
(Continued)

(56) References Cited

U.S. PATENT DOCUMENTS 4,040,427 A * 8/1977 Winnie ................. A61M 25/02
  604/180
4,134,159 A * 1/1979 Wilson ..................... A61F 2/60
  623/27
(Continued)

FOREIGN PATENT DOCUMENTS

DE 3006472 A1 9/1980
DE 10316726 A1 1/2005
(Continued)

OTHER PUBLICATIONS

Heinlin, Julia, et al., "Plasma Medicine: Possible Applications in Dermatology," JDDG Ubersichtsarbeit, Dec. 2010 (Band 8), pp. 968-977.

(Continued)

*Primary Examiner* — Andrew M Gilbert
(74) *Attorney, Agent, or Firm* — Holland & Hart, LLP

(57) ABSTRACT

A transcutaneous connection between an exterior and an interior of a human or animal body includes a cylindrical skin penetration piece which provides a passage through the skin and has a longitudinal axis that determines the direction of passage through the skin. Wound-healing action and reliable disinfection are effected using an annular flat electrode arrangement, which has a contact surface at an angle to the longitudinal axis, can be fastened to the skin penetration piece. The electrode arrangement includes a flat electrode and a flat dielectric shielding the electrode relative to (Continued)

the surface of the skin, and is designed as a counter-electrode to generate a dielectric barrier plasma between the dielectric and the surface of the skin.

25 Claims, 4 Drawing Sheets

(51) Int. Cl.
| | |
|---|---|
| A61M 1/00 | (2006.01) |
| A61L 2/00 | (2006.01) |
| A61L 2/14 | (2006.01) |
| H05H 1/24 | (2006.01) |
| A61F 2/00 | (2006.01) |
| A61N 1/40 | (2006.01) |
| A61F 2/60 | (2006.01) |
| A61F 2/70 | (2006.01) |
| A61B 18/00 | (2006.01) |

(52) U.S. Cl.
CPC ............ *A61L 2/14* (2013.01); *A61M 1/0088* (2013.01); *H05H 1/2406* (2013.01); *A61B 2018/00583* (2013.01); *A61F 2/60* (2013.01); *A61F 2/70* (2013.01); *A61F 2002/7887* (2013.01); *A61N 1/40* (2013.01); *H05H 2001/2412* (2013.01); *H05H 2001/2418* (2013.01); *H05H 2001/2462* (2013.01); *H05H 2245/1225* (2013.01); *H05H 2277/10* (2013.01)

(58) Field of Classification Search
CPC ........ H05H 2001/2462; A61M 1/0088; A61M 25/0273; A61M 2025/0246; A61M 2025/0273
See application file for complete search history.

(56) References Cited

U.S. PATENT DOCUMENTS

| | | | |
|---|---|---|---|
| 4,281,659 A * | 8/1981 | Farrar | A61B 5/0448 |
| | | | 204/403.02 |
| 4,336,811 A | 6/1982 | Beck et al. | |
| 4,781,720 A * | 11/1988 | Sherva-Parker | A61F 2/2814 |
| | | | 623/27 |
| 4,915,694 A * | 4/1990 | Yamamoto | A61M 25/02 |
| | | | 604/180 |
| 5,207,652 A * | 5/1993 | Kay | A61M 25/02 |
| | | | 128/DIG. 26 |
| 5,226,918 A * | 7/1993 | Silagy | A61F 2/60 |
| | | | 623/27 |
| 5,569,207 A * | 10/1996 | Gisselberg | A61M 25/02 |
| | | | 128/DIG. 26 |
| 5,662,715 A * | 9/1997 | Slemker | A61F 2/76 |
| | | | 623/33 |
| 5,665,477 A * | 9/1997 | Meathrel | A61B 5/04087 |
| | | | 427/2.12 |
| 5,759,206 A * | 6/1998 | Bassett | A61F 2/76 |
| | | | 403/113 |
| 5,833,666 A * | 11/1998 | Davis | A61M 25/02 |
| | | | 604/180 |
| 5,888,216 A * | 3/1999 | Haberman | A61F 2/7812 |
| | | | 623/36 |
| 5,944,017 A * | 8/1999 | Tweedle | A61F 15/008 |
| | | | 128/888 |
| 6,571,395 B1 * | 6/2003 | Korkor | A41D 13/1245 |
| | | | 2/104 |
| 8,109,927 B2 * | 2/2012 | Kelly | A61B 18/1477 |
| | | | 606/41 |
| 8,444,701 B2 * | 5/2013 | Bloebaum | A61F 2/2814 |
| | | | 623/32 |
| 8,915,970 B2 * | 12/2014 | Porter | A61F 2/78 |
| | | | 623/16.11 |
| 9,056,148 B2 * | 6/2015 | Zawoy | A61B 7/02 |
| 9,561,135 B2 * | 2/2017 | Robinson | A61F 13/00068 |
| 9,821,150 B2 * | 11/2017 | Pamment | A61M 39/0208 |
| 9,950,106 B2 * | 4/2018 | Isch | A61M 5/001 |
| 2002/0138068 A1 * | 9/2002 | Watson | A61M 39/0208 |
| | | | 604/891.1 |
| 2003/0171825 A1 * | 9/2003 | Blunn | A61C 8/0018 |
| | | | 623/32 |
| 2004/0193286 A1 * | 9/2004 | Grundei | A61F 2/60 |
| | | | 623/24 |
| 2004/0210195 A1 * | 10/2004 | Affeld | A61B 17/60 |
| | | | 604/171 |
| 2004/0243251 A1 * | 12/2004 | Carstens | A61F 2/7812 |
| | | | 623/34 |
| 2005/0089363 A1 * | 4/2005 | Curtis | A61F 2/76 |
| | | | 403/362 |
| 2007/0060891 A1 * | 3/2007 | Skiera | A61F 2/2814 |
| | | | 604/175 |
| 2007/0225652 A1 * | 9/2007 | Scherr | A61M 25/02 |
| | | | 604/180 |
| 2008/0060891 A1 * | 3/2008 | Chen | F16D 65/122 |
| | | | 188/218 XL |
| 2008/0281421 A1 * | 11/2008 | Cahn | A61L 27/24 |
| | | | 623/15.12 |
| 2010/0145253 A1 * | 6/2010 | Gutsol | A61B 18/042 |
| | | | 604/20 |
| 2010/0174246 A1 * | 7/2010 | Bunch | A61M 25/09 |
| | | | 604/265 |
| 2010/0174346 A1 * | 7/2010 | Boyden | A61F 2/30 |
| | | | 607/113 |
| 2011/0022043 A1 * | 1/2011 | Wandke | A61N 1/40 |
| | | | 606/41 |
| 2011/0052664 A1 * | 3/2011 | Tennican | A61F 13/00 |
| | | | 424/445 |
| 2012/0035734 A1 * | 2/2012 | Unwin | A61F 2/32 |
| | | | 623/20.14 |
| 2012/0046602 A1 * | 2/2012 | Morfill | A61L 2/0011 |
| | | | 604/23 |
| 2012/0259270 A1 * | 10/2012 | Wandke | A61N 1/0408 |
| | | | 604/23 |
| 2012/0271225 A1 * | 10/2012 | Stieber | A61B 18/042 |
| | | | 604/26 |
| 2013/0345620 A1 * | 12/2013 | Zemel | A61B 18/042 |
| | | | 604/24 |
| 2014/0081422 A1 * | 3/2014 | Hugate | A61F 2/2814 |
| | | | 623/32 |
| 2014/0081442 A1 * | 3/2014 | Chang | G06F 17/50 |
| | | | 700/108 |
| 2014/0182879 A1 * | 7/2014 | Busse | A61N 1/40 |
| | | | 174/98 |
| 2014/0188058 A1 * | 7/2014 | Robinson | A61F 13/00068 |
| | | | 604/319 |
| 2015/0037201 A1 * | 2/2015 | Armour | A61B 19/38 |
| | | | 422/3 |
| 2015/0038584 A1 * | 2/2015 | Fridman | A01N 37/46 |
| | | | 514/562 |
| 2015/0157870 A1 * | 6/2015 | Kalghatgi | A61N 1/44 |
| | | | 604/23 |

FOREIGN PATENT DOCUMENTS

| | | |
|---|---|---|
| DE | 102007030915 A1 | 1/2009 |
| DE | 102009002278 A1 | 10/2010 |
| DE | 202009011521 U1 | 12/2010 |
| WO | 2011076193 A1 | 6/2011 |
| WO | 2012096965 A1 | 7/2012 |

OTHER PUBLICATIONS

PCT International Search Report for PCT International Patent Application No. PCT/DE2013/000437, dated Mar. 25, 2014.

* cited by examiner

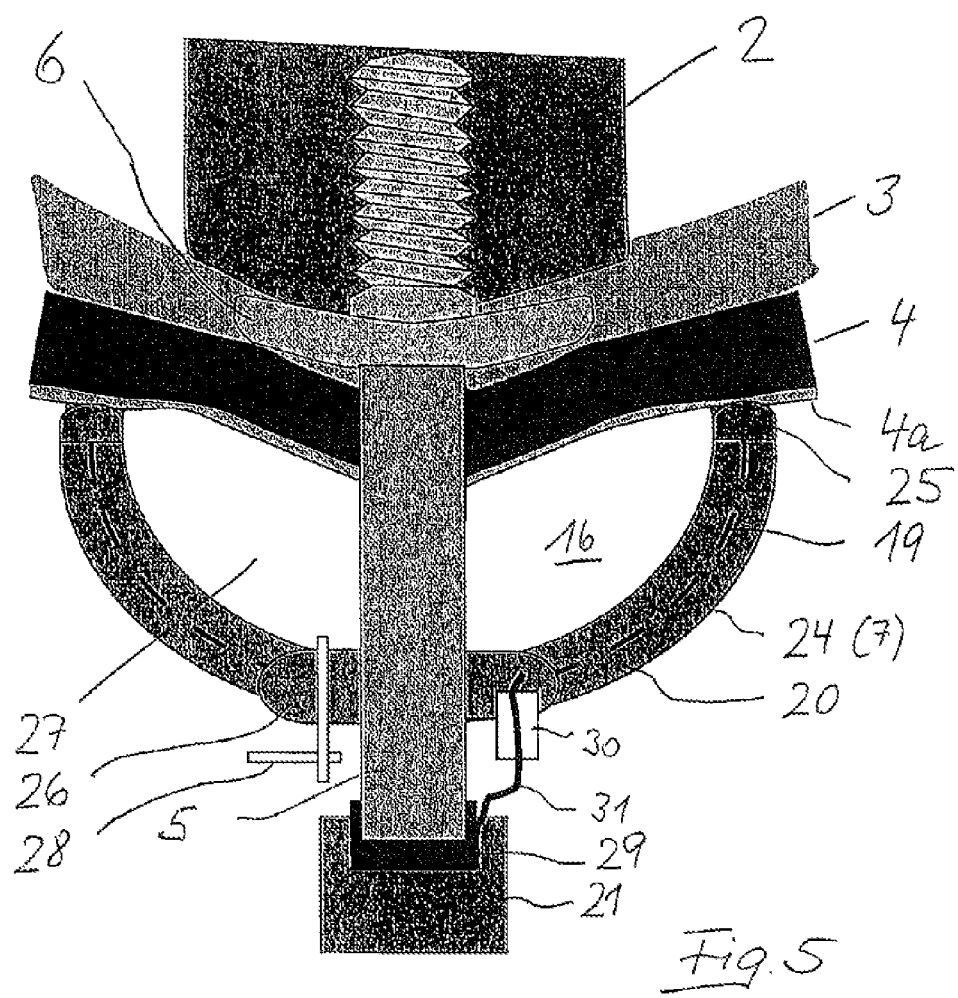

ND DEVICE FOR PRODUCING A TRANSCUTANEOUS CONNECTION

ELECTRODE ARRANGEMENT FOR PLASMA TREATMENT AND DEVICE FOR PRODUCING A TRANSCUTANEOUS CONNECTION

TECHNICAL FIELD

The invention relates to an electrode arrangement for an antiseptic dielectric barrier discharge plasma treatment of a wound area on a skin surface, comprising a planar electrode and a dielectric embodied as a planar material, wherein the planar electrode is fastened to the dielectric in such a way that a layer of the dielectric shields the electrode from the skin surface.

BACHGROUND

It is known that the skin of the human or animal body can be treated by cold plasma in order to generate different effects. A substantial effect lies in the antiseptic effect of the ionized gas that forms the plasma. The antiseptic effect can, in particular, promote wound healing since the wound healing can be impeded by germs, in particular streptococci. Moreover, it appears to be possible to treat skin infections using a plasma (Heinlin et al.: "Plasmamedizin: Anwendungsmöglichkeiten in der Dermatologie" [Plasma medicine: Application options in dermatology] in JDDG 12-2010 (volume 8) pages 968-977).

Very different arrangements have been disclosed for generating plasma for treating the skin surface.

A commonly applied embodiment provides for the generation of a so-called plasma jet, in which the plasma is generated within a rod-shaped housing. The housing forms an applicator tip, from which the ionized gas emerges as a plasma beam and is projected onto the skin. The instrument can be held and guided like a ballpoint pen in order to successively expose the skin surface to be treated to the ion beam which tends to be incident in a punctiform manner.

Moreover, DE 10 2007 030 915 A1 has disclosed the practice of forming hollow fibers from a dielectric substance, which hollow fibers are provided in the interior thereof with a metallically conducting coating such that the hollow fiber forms a dielectric with an internal shielded electrode which, together with the surface of a conducting body, for example the skin surface, serving as a counter electrode, may form a plasma field. Here, provision is also made for forming a web using the hollow fibers which can be placed in a planar manner on an irregular surface, in particular the skin surface of the human body. The advantage of an electrode arrangement that can be adapted to the irregular topology of the skin surface for performing a plasma treatment is generated hereby.

WO 2011/076193 A1 has furthermore disclosed a flexible planar electrode arrangement of the type set forth at the outset. Here, the dielectric is formed by a flexible planar material which shields a planar flexible electrode from the surface to be treated when the dielectric lies on the surface to be treated. On the side pointing toward the surface to be treated, the dielectric is provided with a structure for forming air guiding regions in which the plasma is generated during the treatment, i.e. directly on the skin surface. In the process, the planar electrode can be embedded in the dielectric and only protrudes from the dielectric with an electrical high-voltage connector. Shielding in relation to the skin surface is realized by this embedding. Therefore, the embedding can be substantially on one side, but also on all sides.

For the purposes of fastening exoprostheses, i.e. prostheses which replace an amputated body part, it is conventional to form a prosthesis shank which engages over the remaining amputation stump of the amputated body part and which is fastened there, for example with the aid of negative pressure. This type of fastening of prostheses leads to problems if there is a change in the soft tissue structure in the amputation stump. Therefore, the process of performing an osseointegration, i.e. of fastening the exoprosthesis to the bone of the amputation stump, has been proposed. To this end, an adapter, on which the prosthesis can be fastened, must be introduced through the skin into the bone and fastened there. Since the adapter is to be implanted for an unlimited time and must protrude through the skin to the outside, it is important that no germs enter into the interior of the body through the separation point between adapter and skin or soft tissue. Therefore, the assumption is made that the adapter should have a surface which hinders the settlement of germs thereon and for example consists of polished titanium. In the process, it is necessary to disinfect the employed adapter and the region of the skin around the adapter regularly in order thus to prevent the emergence of infections by germs.

For the purposes of stabilizing the adapter in the soft tissue, the practice of inserting the adapter into the amputation stump in such a way that a planar soft tissue anchor surrounds the adapter and forms a large porous perforated surface, through which soft tissue can penetrate, such that the adapter comprising the soft tissue anchor thereof grows into the soft tissue has furthermore been proposed.

Tests have also already been carried out as to whether the growing-in of the adapter, possibly with a soft tissue anchor, can be accelerated and improved using a bioactive coating, for example with hydroxylapatite. In the long-term, such a coating may be helpful, but it does not prevent the problems resulting from possible infections.

Similar problems also exist in the case of other transcutaneous devices, such as e.g. permanent catheters, permanent infusion cannulas etc.

Summary

The present invention is therefore based on the object of simplifying the use of transcutaneous devices in order to highlight an option for simple and permanent disinfection of the skin and tissue region surrounding the transcutaneous device fastened to the body.

According to the invention, this object is achieved by an electrode arrangement of the type set forth at the outset by virtue of the electrode arrangement including a ring-shaped contact surface that is formed by the dielectric and being provided for fastening to a skin penetration piece bringing about skin penetration with a longitudinal axis such that the electrode arrangement surrounds the skin penetration piece and the contact surface is at an angle >20° in relation to the longitudinal axis.

Here, the dielectric can be provided on the side thereof facing the skin surface with a structure for forming air guiding regions when the dielectric lies on the skin surface by way of the structure. Here, the structure is preferably formed by protruding lugs or studs, the surfaces of which form the contact surface.

The dielectric—and hence the planar electrode—may consist of a rigid dielectric material, for example a ceramic. However, for the purposes of contacting the skin surface, it may be advantageous to embody the planar electrode in a flexible manner by virtue of both the electrode itself and the dielectric consisting of a flexible material. The dielectric is preferably a flexible polymer or elastomer.

In order to achieve the stated object, a device of the type set forth at the outside is further, according to the invention, characterized in that a ring-shaped, planar electrode arrangement including a contact surface that is at an angle to the longitudinal axis is fastenable to the skin penetration piece, which electrode arrangement includes the planar electrode and a planar dielectric shielding the planar electrode from the skin surface and is embodied for generating a dielectric barrier discharge plasma between the dielectric and the skin surface as counter electrode.

Therefore, by using the present invention, it is possible to combine a plasma electrode with the transcutaneous adapter in order thereby to be able to generate a suitable plasma field by means of which the skin penetration region and the surroundings thereof on the skin surface can be disinfected in a reliable manner. Here, it is also possible to prevent the emergence of a damaging biofilm on the adapter, even in the skin penetration region. As a result, it is possible to dispense with the previous, possibly damaging use of chemicals, the addition of silver ions, etc. After insertion of the adapter, the plasma electrode device also brings about improved wound healing for the operation wound. The exudate usually emerging after the insertion of the adapter is both reduced and made germ-free by the plasma treatment, and so improved wound healing is made possible by a regular plasma treatment. Here, the electrode arrangement can be permanently connected to the adapter or, in a preferred embodiment, be connectable to the adapter in an easily detachable manner in order thus to be able to be placed onto the adapter for the plasma treatment.

The electrode arrangement surrounds the adapter in a ring-shaped manner. Here, the ring shape need not extend through 360°, but can extend over a partial circle, for example a three-quarter circle or a semicircle in order to simplify the subsequent attachment. The ring-shaped preferably extends over a circumferential angle between $\pi$ and $2\pi$.

The device according to the invention, which includes an adapter for fastening an exoprosthesis, may include all features which were previously found to be expedient for such devices and which have been explained above, for example a polished surface which hinders germs settling thereon, a surface formed with a bioactive coating, a soft tissue anchor, which can likewise be provided with a bioactive coating, etc.

The device according to the invention can also be one of the aforementioned other transcutaneous devices and, by means of the plasma electrode, prevent the ingress of external germs into the body interior or accelerate wound healing. Accordingly, the electrode arrangement according to the invention may also be used in conjunction with transcutaneous cannulas and external fixators. The device for establishing a transcutaneous connection can therefore also comprise a cannula or an external fixator.

An electric control of the electrode arrangement according to the invention or of the device according to the invention can be attached directly on the electrode arrangement. However, it is also possible to provide the control device on e.g. the exoprosthesis itself and, for example, connect said control device to the electrode arrangement by means of plug-in connection when the electrode arrangement is required, by way of example is plugged onto the adapter for use. Here, the mechanical connection between the electrode arrangement and the adapter can be brought about by means of a suitable fastening device. It is particularly advantageous for the electric device to have a flexible embodiment and for the adapter to be provided with a pressure element for pressing the flexible electrode device in the direction of the proximal end of the adapter such that the contact surface of the electric device is pressed against the skin surface. The electrode control can also be embodied in such a way that it brings about a gas supply to the skin surface such that the plasma is primarily not formed by the surrounding air but by the supplied gas. In this manner, the plasma treatment can be accompanied by a supporting therapeutic treatment by means of the supplied gas.

Furthermore, it is possible to embody the plasma as low-pressure plasma if a negative pressure space is formed with the skin surface by means of a bell arrangement. The dielectric barrier discharge plasma is then generable in the negative pressure space under negative pressure. To this end, the bell arrangement can consist of a molded plastic, which is so stable that it maintains the bell shape, even in the case of applied negative pressure. The free edge of the bell arrangement may be sealed with respect to the skin surface by means of a sealing ring.

In a particularly preferred arrangement, the bell arrangement is formed by the dielectric on which the electrode is fastened. The electrode is preferably embedded into the dielectric. Here, the dielectric forming the bell arrangement both has the function of providing the dielectric barrier for the plasma discharge and of forming the negative pressure space with the skin surface.

The invention is intended to be explained in more detail below on the basis of exemplary embodiments depicted in the drawing. In detail:

FIG. 5 shows a sectional illustration of another embodiment of the invention, in which the plasma is generated in a negative pressure space.

Figure 1:
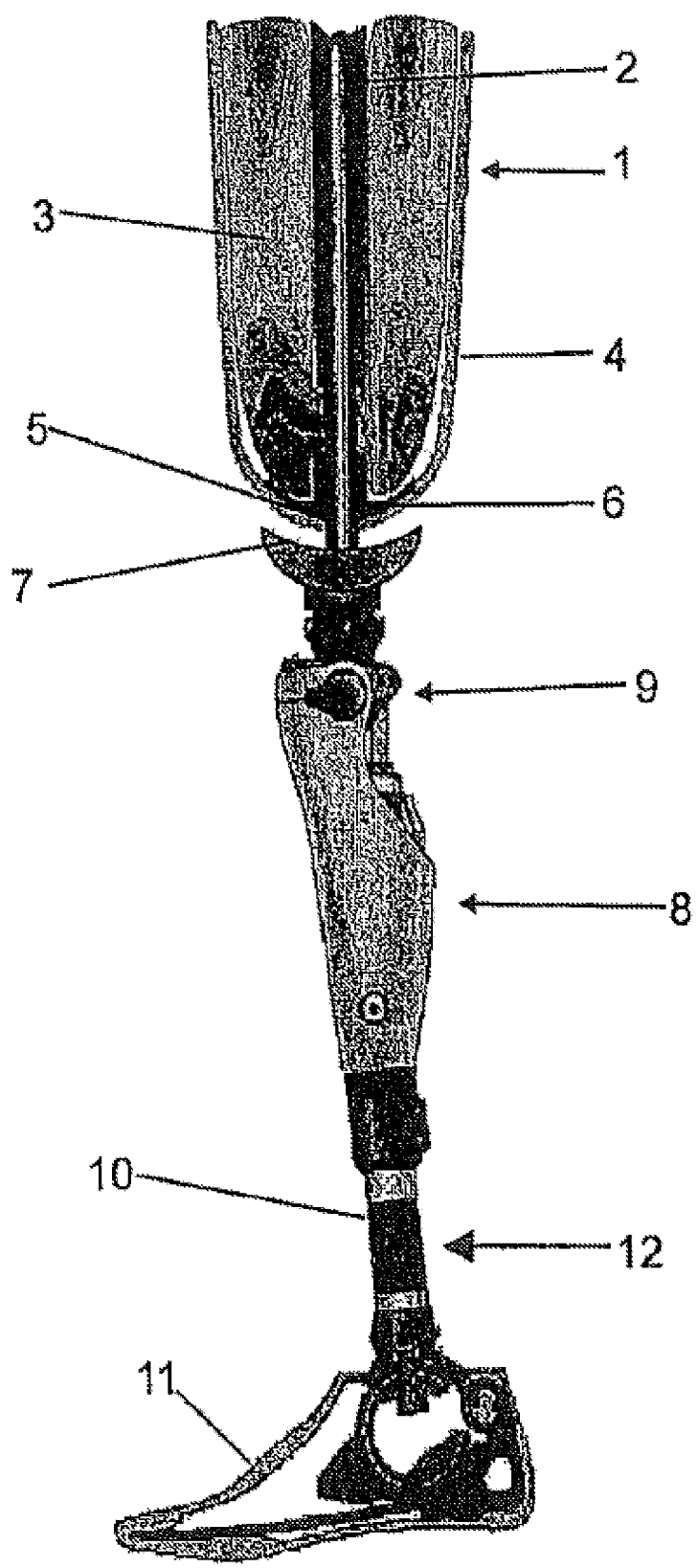
FIG. 1 shows a schematic illustration of a thigh amputation stump, with an exoprosthesis fastened to the bone thereof.

In FIG. 1, it is possible to identify an amputation stump 1 which has arisen as a result of a leg amputation above the knee. From the inside to the outside, the amputation stump consists of a bone 2, namely the residual femur, soft tissue 3 and skin 4.

An adapter 5 forming a skin penetration piece is passed through the skin 4 at the distal end of the amputation stump 1 and attached as an implant in the interior of the bone 2. In the interior of the amputation stump 1, the adapter 5 carries a soft tissue anchor 6 and, outside of the amputation stump 1 and directly adjacent to the skin 4 surrounding the adapter 5, said adapter carries an electrode arrangement 7 for generating a cold, dielectric barrier discharge plasma between the skin 4 and the electrode arrangement 7.

A prosthesis 8, which includes a knee joint 9, a lower leg part 10 and a foot prosthesis 11 fastened in a hinged manner to the lower leg part 10 in the illustrated exemplary embodiment, is fastened to the adapter 5. The basic setup of such prostheses is known and not important to the present invention, and so a more precise description of the details is dispensed with.

In FIG. 1, it is possible to identify that a control 12 with an energy supply for the electrode arrangement is fastened to the lower leg part 10 of the prosthesis 8. However, this arrangement of the control device only constitutes one embodiment option since there are numerous further options for fastening the control device to the prosthesis 8 or to the adapter 5, or for integrating said control device into the electrode arrangement 7.

Figure 2:
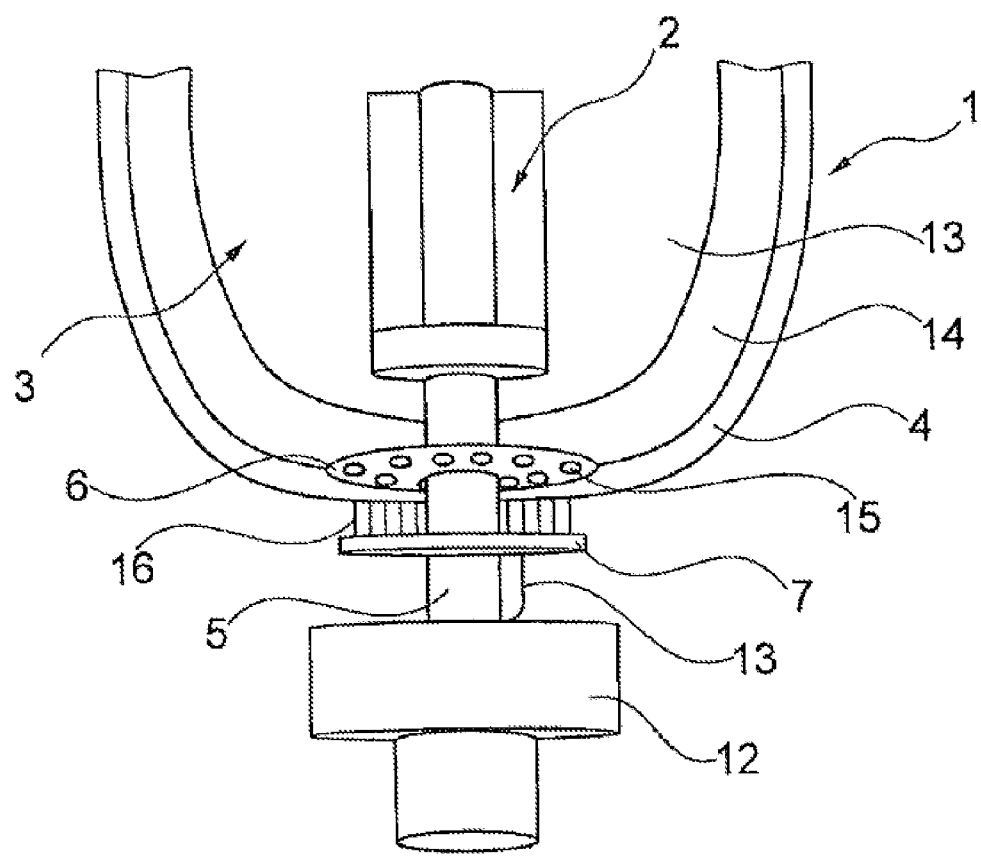
FIG. 2 shows a schematic illustration of the setup of an adapter fastened to the bone, to which adapter the exoprosthesis is fastenable.

FIG. 2 shows a variant of the arrangement from FIG. 1. In the illustration of FIG. 1, the soft tissue 3 surrounding the bone 2 is depicted as muscle tissue 13 and fat tissue 14 or subcutaneous tissue, which is situated directly below the skin 4.

The adapter 5 is formed by a cylindrical tube with a circular cross section and carries the soft tissue anchor 6 below the skin 4, which soft tissue anchor is embodied as a planar disk with slight arcing adapted to the form of the amputation stump 1 at the distal end thereof. There are schematic depictions of passage openings 15 in the planar soft tissue anchor, through which openings the soft tissue can grow in order to assist the growing-in of the soft tissue anchor 15 in the soft tissue 3.

The electrode arrangement 7, which has a planar and flexible design, is situated on the adapter 5 outside of the amputation stump 1. Plasma 16, which is indicated schematically in FIG. 2, is generated between the electrode arrangement 7 and the skin 4 as a counter electrode.

The control 12, which is connected to the electrode arrangement 7 by means of a cable 13, is carried by the adapter in this exemplary embodiment.

In the region of the skin 4 and in the interior of the amputation stump 1, the adapter 5 is provided with a bioactive coating which extends within the amputation stump 1 over at least the majority of the length of the adapter 5 and which eases the growing-in of the adapter 5 into the bone tissue or the soft tissue 3.

Figure 3:
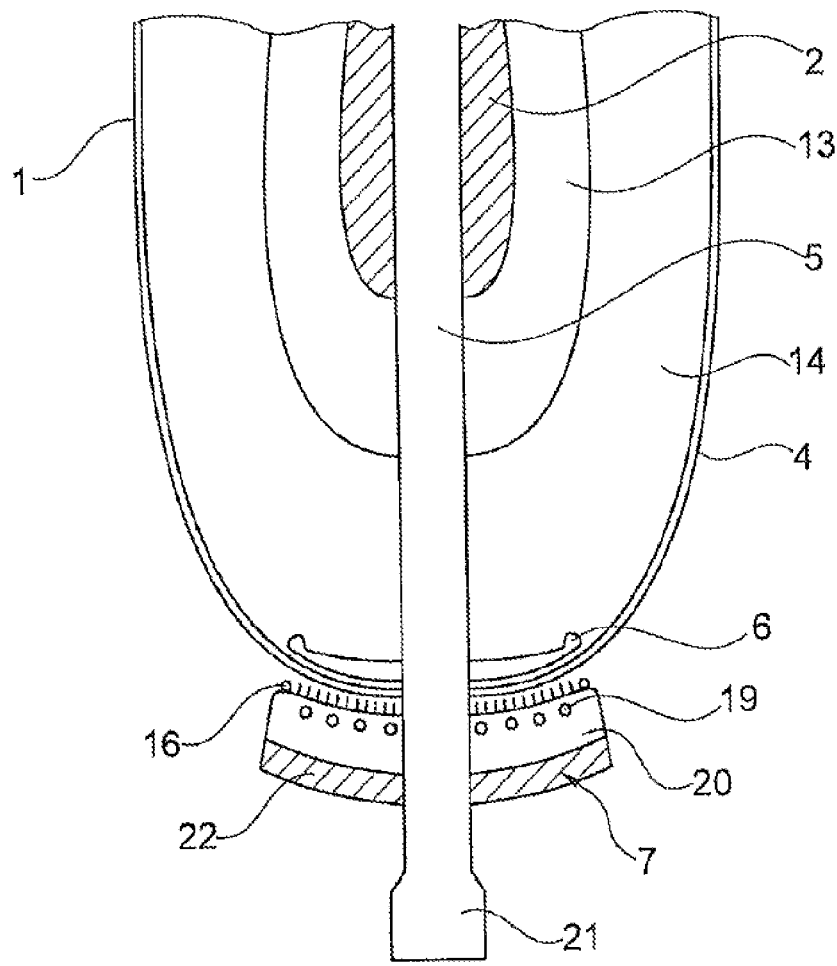
FIG. 3 shows a sectional illustration of a further variant.

In FIG. 3, it is possible to identify the setup of the electrode arrangement 7 in accordance with one exemplary embodiment of the invention.

In the interior of the amputation stump 1, the adapter extends through the skin 4, the fat tissue 14 and the muscle tissue 13 into the bone 2, where it is fastened in a manner conventional for implants. The soft tissue anchor 6 is situated on the inner side of the skin 4, while the electrode arrangement 7 immediately adjoins on the outer side of the skin 4 in order to form the plasma between the electrode arrangement 7 and the skin 4.

The electrode arrangement 7 consists of a flexible electrode 19, which, for example, can be formed by a wire mesh. In the depicted exemplary embodiment, the electrode 19 is molded on all sides into a flexible dielectric 20 such that the electrode 19 is shielded from the skin 4 by the dielectric 20. When a high-voltage AC potential is applied, a continuous current flow between the electrode 19 and the skin 4 is thus prevented and a dielectric barrier plasma discharge sets in, by means of which the plasma 16 is formed.

Preferably, the dielectric 20 is provided with a structure on the surface thereof facing the skin 4, by means of which structure air can collect and move between the skin 4 and the dielectric 20, in which structure the plasma can form when applying a high-voltage to the electrode 19 in relation to the skin 4 as a counter electrode. The structure can preferably consists of individual protruding studs of the dielectric 20, which substantially are embodied with the same height and the end faces of which form a contact surface for the skin 4 at the distal end of the amputation stump 1.

In FIG. 3, it is possible to identify schematically that the adapter 5, at the distal end thereof, is provided with a coupling element 21 by means of which the adapter 5 can be coupled to the prosthesis 8—optionally in an adjustable manner. Such coupling of a prosthesis with a tube-shaped element is known to a person skilled in the art will not be explained in any more detail here.

In this exemplary embodiment, the electrode arrangement 7 is completed by a planar pressure element 22, which is pretensioned in the direction of the skin 4 and by means of which the flexible dielectric 20 and the flexible electrode 19 are areally pretensioned in the direction of the amputation stump 1 such that the flexible electrode arrangement 7 is securely pressed against the distal end of the amputation stump 1 and can, in the process, adapt to possible irregularities in the amputation stump 1 so as to achieve a defined embodiment of a plasma 16.

Figure 4:
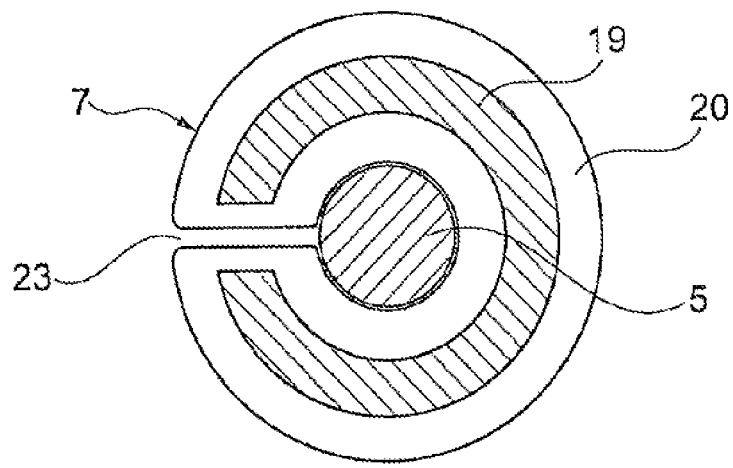
FIG. 4 shows a section through one embodiment of the adapter of an electrode arrangement surrounding the latter.

The plan view on the electrode arrangement 7 in FIG. 4 makes it clear that the electrode arrangement 7 surrounds the adapter 5 as a planar electrode arrangement in a ring-shaped manner. Here, the dielectric 20 is embodied as a ring arrangement provided with a radial slit 23. In conjunction with the flexibility of the electrode arrangement 7, what this slit 23 renders possible is that said electrode arrangement is subsequently arranged around the adapter 5 by deformation. The flexible planar electrode 19, which is e.g. formed by a wire mesh, is surrounded on all sides by the flexible dielectric 20 and merely guided out of the dielectric 20 in an insulated manner at a suitable position thereof in order to supply the electrode 19 with a high voltage, preferably as a high AC voltage, required for forming the plasma 16. Accordingly, the electrode 19 also has a ring-shaped design, but has a smaller width than the dielectric 20. Moreover, the electrode 19 ends at the slit 23 at a distance in front of the end of the dielectric 20 so as to ensure the electrode 19 is embedded into the dielectric 20 on all sides.

FIG. 4 shows a possible exemplary embodiment. Naturally, the slit 23 can also be dispensed with such that the electrode arrangement 7 constitutes a closed ring-shaped arrangement which is fastened to the adapter 5 as such, as a result of which it preferably remains on the adapter 5 in a securely installed manner.

For the purposes of a detachable connection, which enables a subsequent or intermittent attachment of the electrode arrangement 7 on the adapter 5, the slit 23 can also have a substantially larger design such that the electrode arrangement for example constitutes a ¾-, ⅔-circle or the like. Furthermore, it is possible to embody the electrode arrangement with two diametrically opposing slits 23 in order thus to design these in the form of two semi-rings in a subsequently assemblable manner. In other cases, it may be sufficient for the electrode arrangement 7 merely to surrounds the adapter 5 on a partial ring. Here, the electrode arrangement can optionally be fastened in a rotatable manner to the adapter 5 in order thereby to successively generate plasma 16 for mutually adjacent sections of the skin 4 surrounding the adapter 5.

All nonconductive, flexible plastics, preferably those into which the electrode 19 can be embedded by casting, injection molding or the like, are suitable as a dielectric. The embedding need not necessarily occur on all sides but needs to ensure that the electrode 19 is shielded from the skin in order thus to preclude direct current flow from the electrode 19 to the skin 4.

In the depicted exemplary embodiments, the electrode arrangement 7 extends substantially perpendicular to the longitudinal axis of the adapter 5. This arrangement is preferable but not mandatory. Particularly if the electrode arrangement is fastened to a device 5 which does not act as an adapter for a prosthesis 8, it may be expedient for the electrode arrangement 7 to also form an acute angle with the longitudinal axis of the device, wherein the angle should, in any case, be greater than 20°. Here, the angle is defined between the longitudinal axis and a plane of the electrode arrangement 7. In the case of an arced electrode arrangement, this angle is defined by a tangential plane of the electrode arrangement 7 at the point of intersection with the longitudinal axis of the device 5.

FIG. 5 shows a variant of the setup in accordance with FIG. 3, in which the adapter 5 likewise extends into the bone 2, where it is fastened by screwing-in, through the skin 4 and the soft tissue 3. The soft tissue anchor 6 is situated on the inner side of the skin 4. On the outer side, the skin is completed by an epidermis, which forms the skin surface 4a.

A bell arrangement 24 is placed onto the skin surface 4a and sealed in relation to the skin surface by means of a sealing ring 25, which, for example, is made of silicone. The bell arrangement 24 has a dome-like arch and surrounds the adapter 5 on the outside of the skin at the highest point of the arching thereof. A central sealing ring 26 establishes the sealing between the bell arrangement 24 and the adapter 5. Together with the skin surface 4a, the bell arrangement 24 delimits a negative pressure space 27, in which the plasma 16 can form.

In the depicted exemplary embodiment, the bell arrangement is formed by the electrode arrangement 7 by virtue of the dielectric 20 being put into the bell shape and the electrode 19 being embedded into the dielectric 20. Here, the electric 19 preferably consists of a superelastic material, for example a nickel-titanium alloy such as nitinol.

The drawing schematically illustrates that an inlet and outlet valve 28 is passed through the central sealing ring 26, wherein e.g. a (manual or electric) vacuum pump is connectable to said valve.

In the depicted exemplary embodiment, a piezo-element 29 is positioned between the coupling element 21 and the adapter and it optionally generates a supply voltage for the electrode 19 from mechanical loads and it is therefore connected to a voltage controller 30 fastened to the central sealing ring 26 by means of a line 31. It is possible to generate the plasma directly in a pulse-like manner from the voltage pulses supplied by the piezo-element 29 when the latter is loaded.

Embodying the plasma 16 as a low-pressure plasma in the negative pressure space 27 is advantageous in that an intensive contact is established between the surface 4a of the skin and the plasma such that the disinfection and sterilization by the plasma is reliably brought about at all points on the skin surface and at the skin penetration point of the adapter 5.

The invention claimed is:

1. An electrode arrangement for an antiseptic dielectric barrier discharge plasma treatment of an area on a skin surface, comprising:
    a planar electrode;
    a dielectric embodied as a planar material, wherein the planar electrode is fastened to the dielectric in such a way that a layer of the dielectric shields the planar electrode from the skin surface;
    a skin penetration piece providing skin penetration and having a longitudinal axis, a proximal end, and a distal end, the skin penetration piece being configured as an adapter to fasten an exoprosthesis to a bone of a residual limb, the skin penetration piece being connectable to the bone at the proximal end and to the exoprosthesis at the distal end;
    a ring-shaped contact surface that is formed by the dielectric and is provided for fastening to the skin penetration piece, the ring-shaped contact surface facing towards the skin surface when the skin penetration piece is arranged to penetrate the skin surface;
    a barrier discharge plasma positioned between the ring-shaped contact surface and the skin surface;
    wherein the dielectric, together with the planar electrode, surrounds and is permanently connected to the skin penetration piece, the ring-shaped contact surface is at an angle >20° in relation to the longitudinal axis, and the dielectric and the planar electrode have a radial slit formed therein and having a partial circular construction, the radial slit providing mounting of the planar electrode with the dielectric to the skin penetrating piece;
    wherein the electrode arrangement is configured to provide regular treatment of the skin surface while the planar electrode and dielectric are attached to the skin penetration piece.

2. The electrode arrangement as claimed in claim 1, wherein the dielectric includes air guiding regions on a side facing the skin surface when the dielectric lies on the skin surface.

3. The electrode arrangement as claimed in claim 2, wherein protruding lugs form the air guiding regions, wherein surfaces of the protruding lugs form a contact surface to contact the skin surface.

4. The electrode arrangement as claimed in claim 1, wherein the planar electrode is flexible.

5. The electrode arrangement as claimed in claim 1, wherein the ring-shaped contact surface is arranged at an acute angle of >20° and <90° relative to the longitudinal axis.

6. The electrode arrangement as claims in claim 1, wherein the skin penetration piece includes a coupling element positioned at the distal end to connect the skin penetration piece to the exoprosthesis.

7. The electrode arrangement as claimed in claim 6, wherein the coupling element provides an adjustable connection of the skin penetration piece to the exoprosthesis.

8. A device for producing a transcutaneous connection between an exoprosthesis and a bone of a human or animal body, comprising;
    a cylindrical skin penetration piece which causes skin penetration and comprises a proximal end, a distal end, and a longitudinal axis determining the skin penetration direction, the skin penetration piece being configured as an adapter to fasten the exoprosthesis to the bone, the skin penetration piece being connectable to the bone at the proximal end and to the exoprosthesis at the distal end;
    a ring-shaped, planar electrode arrangement including a contact surface that is at an angle to the longitudinal axis, the electrode arrangement being fastenable to the skin penetration piece, the electrode arrangement including a planar electrode and a planar dielectric shielding the planar electrode from a skin surface, the electrode arrangement being configured to generate a dielectric barrier discharge plasma between the dielectric and the skin surface as a counter electrode;
    wherein the dielectric, together with the planar electrode, surrounds and is permanently attached to the skin penetration piece, the entire contact surface of the electrode arrangement is at an acute angle of >20° and <90° in relation to the longitudinal axis, and the dielectric and the planar electrode have a radial slit formed therein, the radial slit providing mounting of the planar electrode with the dielectric to the skin penetration piece;

wherein the electrode arrangement is configured to provide regular treatment of the skin surface while the planar electrode with the dielectric is attached to the skin penetration piece.

9. The device as claimed in claim 8, wherein the adapter includes a soft tissue anchor.

10. The device as claimed in claim 8, wherein the electrode arrangement has a flexible embodiment and the adapter is provided with a pressure element for pressing the flexible electrode arrangement in the direction of the proximal end of the adapter.

11. The device as claimed in claim 8, wherein the adapter consists of polished titanium.

12. The device as claimed in claim 8, wherein the skin penetration piece is provided with a bioactive coating.

13. The device as claimed in claim 8, wherein the planar electrode is embedded in the dielectric.

14. The device as claimed in claim 8, wherein a bell arrangement is used to form a negative pressure space with the skin surface, within which space the dielectric barrier discharge plasma is generable in a negative pressure.

15. The device as claimed in claim 14, wherein the bell arrangement comprises a molded plastic and is sealed at a free edge with respect to the skin surface using a sealing ring.

16. The device as claimed in claim 14, wherein the bell arrangement is formed by the dielectric which carries the planar electrode.

17. The device as claimed in claim 8, wherein the bioactive coating comprises hydroxylapatite.

18. An electrode arrangement for an antiseptic dielectric barrier discharge plasma treatment of an area on a skin surface, comprising:
a dielectric having a ring-shaped contact surface;
a flexible electrode fastened to the dielectric in such a way that a layer of the dielectric shields the electrode from the skin surface;
a skin penetration piece providing skin penetration and having a proximal end, a distal end, and a longitudinal axis, the skin penetration piece being fastened to the ring-shaped contact surface and including a pressure element to press the electrode toward the skin surface, the skin penetration piece being configured as an adapter to fasten an exoprosthesis to a bone of a residual limb, the skin penetration piece being connectable to the bone at the proximal end and to the exoprosthesis at the distal end;
a barrier discharge plasma positioned between the ring-shaped contact surface and the skin surface;
wherein the electrode and dielectric surround and are permanently connected to the skin penetration piece, the entire ring-shaped contact surface is arranged at an acute angle of >20° and <90° relative to the longitudinal axis, and the ring-shaped contact surface faces towards the skin surface when the skin penetration piece is arranged to penetrate the skin surface;
wherein the electrode arrangement is configured to provide regular treatment of the skin surface while the electrode and dielectric are attached to the skin penetration piece.

19. The electrode arrangement as claimed in claim 18, wherein a side of the dielectric arranged facing the skin surface comprises air guiding regions when the dielectric contacts the skin surface.

20. The electrode arrangement as claimed in claim 19, wherein the air guiding regions are formed by protruding lugs having surfaces which provide interface with the skin surface.

21. The electrode arrangement as claimed in claim 18, wherein the electrode arrangement is configured to disinfect the skin surface as well as a skin penetration region, the skin penetration region including a channel through which the skin penetration piece penetrates the skin surface.

22. The electrode arrangement as claimed in claim 18, wherein the planar electrode is mounted to the adapter by deformation of the planar electrode.

23. An electrode arrangement for an antiseptic dielectric barrier discharge plasma treatment of an area on a skin surface, comprising:
a planar electrode;
a dielectric embodied as a planar material, wherein the planar electrode is fastened to the dielectric in such a way that a layer of the dielectric shields the planar electrode from the skin surface;
a skin penetration piece providing skin penetration and having a longitudinal axis, a proximal end, a distal end, and a transcutaneous cannula, the skin penetration piece being configured as an adapter to fasten an exoprosthesis to a bone of a residual limb, the skin penetration piece being connectable to the bone at the proximal end and to the exoprosthesis at the distal end;
a ring-shaped contact surface that is formed by the dielectric and is provided for fastening to the skin penetration piece, the ring-shaped contact surface facing towards the skin surface when the skin penetration piece is arranged to penetrate the skin surface;
a barrier discharge plasma positioned between the ring-shaped contact surface and the skin surface;
wherein the dielectric, together with the planar electrode, surrounds and is permanently connected to the skin penetration piece, and the entire ring-shaped contact surface is arranged at an acute angle of >20° and <90° relative to the longitudinal axis;
wherein the electrode arrangement is configured to provide regular treatment of the skin surface while the planar electrode and dielectric are attached to the skin penetration piece.

24. An electrode arrangement for an antiseptic dielectric barrier discharge plasma treatment of an area on a skin surface, comprising:
a planar electrode;
a dielectric embodied as a planar material, wherein the planar electrode is fastened to the dielectric in such a way that a layer of the dielectric shields the planar electrode from the skin surface;
a skin penetration piece providing skin penetration and having a distal end, a proximal end, and a longitudinal axis, the skin penetration piece being configured as an adapter to fasten an exoprosthesis to a bone of a residual limb, the skin penetration piece being connectable to the bone at the proximal end and to the exoprosthesis at the distal end;
a ring-shaped contact surface that is formed by the dielectric and is provided for fastening to the skin penetration piece, the ring-shaped contact surface facing towards the skin surface when the skin penetration piece is arranged to penetrate the skin surface;
a barrier discharge plasma positioned between the ring-shaped contact surface and the skin surface;
wherein the dielectric, together with the planar electrode, surrounds and is permanently connected to the skin penetration piece, the ring-shaped contact surface is at an angle >20° relative to the longitudinal axis;

wherein the electrode arrangement is configured to disinfect the skin surface as well as a skin penetration region, the skin penetration region including a channel through which the skin penetration piece penetrates the skin surface;

wherein the electrode arrangement is configured to provide regular treatment of the skin surface while the planar electrode and dielectric are attached to the skin penetration piece.

25. The electrode arrangement as claimed in claim 24, wherein the dielectric and the planar electrode have a radial slit formed therein, the radial slit providing mounting of the dielectric and the planar electrode to the skin penetration piece.

\* \* \* \* \*